US009282929B2

(12) United States Patent
Choi et al.

(10) Patent No.: US 9,282,929 B2
(45) Date of Patent: Mar. 15, 2016

(54) APPARATUS AND METHOD FOR ESTIMATING MALIGNANT TUMOR

(71) Applicants: SAMSUNG ELECTRONICS CO., LTD., Suwon-si (KR); KOREA ADVANCED INSTITUTE OF SCIENCE AND TECHNOLOGY, Daejeon-si (KR)

(72) Inventors: Choong Hwan Choi, Suwon-si (KR); Yong-man Ro, Daejeon (KR); Dokwan Oh, Suwon-si (KR); Dae-hoe Kim, Daejeon (KR); Jae-young Choi, Daejeon (KR); Woosup Han, Yongin-si (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

(*) Notice: Subject to any disclaimer, the term of this patent is extended or adjusted under 35 U.S.C. 154(b) by 222 days.

(21) Appl. No.: 14/031,093

(22) Filed: Sep. 19, 2013

(65) Prior Publication Data

US 2014/0200433 A1    Jul. 17, 2014

(30) Foreign Application Priority Data

Jan. 16, 2013  (KR) .................. 10-2013-0005120

(51) Int. Cl.
*A61B 5/00* (2006.01)
*G06T 7/00* (2006.01)
(Continued)

(52) U.S. Cl.
CPC .............. *A61B 5/4887* (2013.01); *A61B 5/004* (2013.01); *G06K 9/4604* (2013.01); *G06K 9/6292* (2013.01); *G06T 7/0012* (2013.01); *G06K 2009/4666* (2013.01); *G06T 2207/10072* (2013.01); *G06T 2207/10116* (2013.01); *G06T 2207/10132* (2013.01); *G06T 2207/30068* (2013.01)

(58) Field of Classification Search
CPC ................ A61B 5/004; A61B 5/4887; G06K 2009/4666; G06K 9/4604; G06K 9/6292
See application file for complete search history.

(56) References Cited

U.S. PATENT DOCUMENTS 5,579,360 A   11/1996  Abdel-Mottaleb
6,075,879 A    6/2000  Roehrig et al.
(Continued)

FOREIGN PATENT DOCUMENTS

KR      1020070091714 A       9/2007

OTHER PUBLICATIONS

Choi, J. Y. et al, "Combining multiple feature representations and adaboost ensemble learning for reducing false-positive detections in computer-aided detection of masses on mammograms," 34th Annual International Conference of the IEEE Engineering in Medicine and Biology Society (EMBC), Aug. 28,-Sep. 1, 2012, pp. 4394-4397.

*Primary Examiner* — Baisakhi Roy
(74) *Attorney, Agent, or Firm* — Sughrue Mion, PLLC (57) ABSTRACT

An apparatus for estimating a malignant tumor includes: a segmentor configured to segment a first medical image of an object into a first ROI including a mass and a second medical image of the object into a second ROI including a mass; an interest region determiner configured to acquire a first matched ROI and a second matched ROI, which is matched to the first matched ROI based on location information of the first ROI and the second ROI, respectively; a feature extractor configured to extract a similar feature indicating a degree of similarity between the first matched ROI and the second matched ROI, from the first matched ROI and the second matched ROI; and a classifier configured to generate malignant tumor information indicating whether the mass included in the first matched ROI and the second matched ROI is the malignant tumor, based on the extracted similar feature.

19 Claims, 8 Drawing Sheets

(51) Int. Cl.
*G06K 9/46* (2006.01)
*G06K 9/62* (2006.01)

(56) References Cited

U.S. PATENT DOCUMENTS

| | | | |
|---|---|---|---|
| 7,499,578 B2 * | 3/2009 | Reeves et al. | 382/131 |
| 8,923,952 B2 * | 12/2014 | O'Connor et al. | 600/431 |
| 2002/0172403 A1 * | 11/2002 | Doi et al. | 382/128 |
| 2004/0252870 A1 * | 12/2004 | Reeves et al. | 382/128 |
| 2008/0205717 A1 * | 8/2008 | Reeves et al. | 382/128 |
| 2010/0284586 A1 * | 11/2010 | Elter et al. | 382/128 |
| 2012/0088981 A1 | 4/2012 | Liu et al. | |
| 2013/0216113 A1 * | 8/2013 | O'Connor | 382/128 |
| 2014/0029817 A1 * | 1/2014 | Gleichman et al. | 382/131 |

* cited by examiner

| Feature name | Dims. |
|---|---|
| Difference of shape including NRL | 13 |
| Difference of intensity | 5 |
| Difference of RLS | 20 |
| Difference of GLDS | 24 |
| Difference of SGLD (distance=1) | 52 |
| Difference of SGLD (distance= 1,2,4) | 156 |
| Difference of SGLD (1,2,4,6,8,10) | 312 |
| Difference of LBP(8,1) | 118 |
| Difference of LBP(8,2) | 118 |
| Difference of LBP(8,3) | 118 |
| Difference of Texture flow field | 4 |
| Difference of entropy | |
| Difference of radial distance | |
| Histogram correlation | 6 |
| Intensity correlation | |
| Difference of single-view score | |
| Single-view score of corresponding ROI | |

NRL : Normalized radial length, RLS : Run length statistics, GLDS : Gray level difference statistics,
SGLD : Spatial gray level dependence, LBP : Local binary pattern

APPARATUS AND METHOD FOR ESTIMATING MALIGNANT TUMOR

CROSS-REFERENCE TO RELATED PATENT APPLICATION

This application claims priority from Korean Patent Application No. 10-2013-0005120, filed on Jan. 16, 2013, in the Korean Intellectual Property Office, the disclosure of which is incorporated herein in its entirety by reference.

BACKGROUND

1. Field

Methods and apparatuses consistent with exemplary embodiments relate to estimating a malignant tumor in an object, and more particularly, to analyzing medical images of an object to estimate a malignant tumor.

2. Description of the Related Art

A probability that a woman develops breast cancer at some point in her life is more than 8%. At present, the most effective method of diagnosing breast cancer at an early stage is by a mammography image.

A mammography image may include a lump-like mass, and a medical professional may detect the mass and determine whether the detected mass is benign or malignant.

The accuracy of mammography image analysis depends on the experience and knowledge of the medical professional, and an accuracy of 65% to 75% is possible.

A device for analyzing a mammography image to determine whether a malignant tumor exists in the mammography image may use computer-aided diagnosis (CADx), and when a medical professional performs analysis using a CADx system, accuracy of the analysis may increase. However, the related art CADx system may miss detecting a feature suitable for determining a presence of malignant tumor.

Thus, an efficient CADx system is needed to increase the accuracy of a mammography image analysis.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

One or more exemplary embodiments provide a malignant tumor estimating apparatus and method for increasing accuracy in estimation of a malignant tumor by analyzing a first medical image and a second medical image of an object to estimate whether a malignant tumor is in the object.

According to an aspect of an exemplary embodiment, there is provided an apparatus for estimating a malignant tumor, the apparatus including: a segmentor for segmenting a first medical image of an object into at least one first region of interest (ROI) including a mass and segmenting a second medical image of the object into at least one second ROI including a mass; an interest region determiner for acquiring a first matched ROI from the at least one first ROI and acquiring a second matched ROI from the at least one second ROI, based on location information of the at least one first ROI and the at least one second ROI; a feature extractor for extracting at least one similar feature indicating a degree of similarity between the first matched ROI and the second matched ROI from the first matched ROI and the second matched ROI; and a classifier for generating malignant tumor information indicating whether a mass included in the first matched ROI and the second matched ROI is a malignant tumor, based on the extracted at least one similar feature.

The interest region determiner may acquire the first matched ROI and the second matched ROI which exist at a same location of the object.

The classifier may divide the extracted at least one similar feature into a plurality of groups and include: a plurality of first classifiers for generating a plurality of pieces of malignant tumor preparation information indicating whether the mass included in the first matched ROI and the second matched ROI is a malignant tumor by analyzing a similar feature included in each of the plurality of groups; and a second classifier for generating the malignant tumor information by combining the plurality of pieces of malignant tumor preparation information and reliabilities of the plurality of first classifiers.

The reliability of each of the plurality of first classifiers may be determined in a learning operation of the plurality of first classifiers.

The classifier may determine a degree of similarity between the first matched ROI and the second matched ROI from the extracted at least one similar feature and may determine that the mass included in the first matched ROI and the second matched ROI is a malignant tumor if the degree of similarity is greater than a predetermined reference value.

The apparatus may further include a pre-processor for pre-processing the first medical image and the second medical image to adjust a contrast or brightness of the first medical image and the second medical image.

The feature extractor may extract at least one first feature from a first non-matched ROI except for the first matched ROI from among the at least one first ROI and extract at least one second feature from a second non-matched ROI except for the second matched ROI from among the at least one second ROI, and the classifier may determine based on the at least one first feature whether a mass included in the first non-matched ROI is a malignant tumor and may determine based on the at least one second feature whether a mass included in the second non-matched ROI is a malignant tumor.

The apparatus may further include a display for displaying a first mark on a part corresponding to the first non-matched ROI in the first medical image when the mass included in the first non-matched ROI is determined as a malignant tumor, displaying the first mark on a part corresponding to the second non-matched ROI in the second medical image when the mass included in the second non-matched ROI is determined as a malignant tumor, and displaying a second mark other than the first mark on a part corresponding to each of the first matched ROI and the second matched ROI in the first medical image and the second medical image when the mass included in the first matched ROI and the second matched ROI is determined as a malignant tumor.

The first medical image may include a cranio-caudal (CC) image of a breast, and the second medical image may include a mediolateral oblique (MLO) image of the breast.

The interest region determiner may acquire the location information of the at least one first ROI by using a location relationship between a nipple in the CC image and the at least one first ROI and may acquire the location information of the at least one second ROI by using a location relationship between a nipple in the MLO image and the at least one second ROI.

According to another aspect of an exemplary embodiment, there is provided a method of estimating a malignant tumor by a malignant tumor estimating apparatus, the method including: segmenting a first medical image of an object into at least one first ROI including a mass and segmenting a second medical image of the object into at least one second ROI including a mass; acquiring a first matched ROI from the at least one first ROI and acquiring a second matched ROI from the at least one second ROI, based on location information of the at least one first ROI and the at least one second ROI; extracting at least one similar feature indicating a degree of similarity between the first matched ROI and the second matched ROI from the first matched ROI and the second matched ROI; and generating malignant tumor information indicating whether a mass included in the first matched ROI and the second matched ROI is a malignant tumor, based on the extracted at least one similar feature.

The acquiring of the first matched ROI and the second matched ROI may include acquiring the first matched ROI and the second matched ROI which exist at a same location of the object.

The generating of the malignant tumor information may include: dividing the extracted at least one similar feature into a plurality of groups; respectively generating, by a plurality of first classifiers included in the malignant tumor estimating apparatus, a plurality of pieces of malignant tumor preparation information indicating whether the mass included in the first matched ROI and the second matched ROI is a malignant tumor by analyzing a similar feature included in each of the plurality of groups; and generating, by a second classifier included in the malignant tumor estimating apparatus, the malignant tumor information by combining the plurality of pieces of malignant tumor preparation information and reliabilities of the plurality of first classifiers.

The reliability of each of the plurality of first classifiers may be determined in a learning operation of the plurality of first classifiers.

The generating of the malignant tumor information may include: determining a degree of similarity between the first matched ROI and the second matched ROI from the extracted at least one similar feature; and determining that the mass included in the first matched ROI and the second matched ROI is a malignant tumor if the degree of similarity is greater than a predetermined reference value.

The method may further include pre-processing the first medical image and the second medical image to adjust a contrast or brightness of the first medical image and the second medical image.

The method may further include: extracting at least one first feature from a first non-matched ROI except for the first matched ROI from among the at least one first ROI and extracting at least one second feature from a second non-matched ROI except for the second matched ROI from among the at least one second ROI; and determining based on the at least one first feature whether a mass included in the first non-matched ROI is a malignant tumor and determining based on the at least one second feature whether a mass included in the second non-matched ROI is a malignant tumor.

The method may further include: displaying a first mark on a part corresponding to the first non-matched ROI in the first medical image when the mass included in the first non-matched ROI is determined as a malignant tumor and displaying the first mark on a part corresponding to the second non-matched ROI in the second medical image when the mass included in the second non-matched ROI is determined as a malignant tumor; and displaying a second mark other than the first mark on a part corresponding to each of the first matched ROI and the second matched ROI in the first medical image and the second medical image when the mass included in the first matched ROI and the second matched ROI is determined as a malignant tumor.

The first medical image may include a cranio-caudal (CC) image of a breast, and the second medical image may include a mediolateral oblique (MLO) image of the breast.

The location information of the at least one first ROI may be acquired by using a location relationship between a nipple in the CC image and the at least one first ROI, and the location information of the at least one second ROI may be acquired by using a location relationship between a nipple in the MLO image and the at least one second ROI.

According to another aspect of an exemplary embodiment, there is provided a non-transitory computer-readable storage medium having stored therein program instructions, which when executed by a computer, perform the method.

BRIEF DESCRIPTION OF THE DRAWINGS

The above and/or other aspects will become more apparent by describing certain exemplary embodiments with reference to the accompanying drawings, in which.

DETAILED DESCRIPTION

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The term 'unit' used in the exemplary embodiments indicates a component including software or hardware, such as a Field Programmable Gate Array (FPGA) or an Application-Specific Integrated Circuit (ASIC), and the unit performs certain roles. However, the unit is not limited to software or hardware. The unit may be configured to be included in an addressable storage medium or to be implemented using one or more processors. Therefore, for example, the unit includes components, such as software components, object-oriented software components, class components, and task components, processes, functions, attributes, procedures, subroutines, segments of program code, drivers, firmware, microcode, circuits, data, a database, data structures, tables, arrays, and variables. A function provided inside components and 'units' may combine them into a smaller number of components and units or further divide them into additional components and units.

In the specification, the term 'object' may refer to a human or to a part of a human body or an animal. For example, the object may include an organ, such as a liver, a heart, a womb, a brain, a breast, an abdomen, or the like, or blood.

In addition, in the specification, the medical image may include an X-ray image, an ultrasound image, a computed tomography (CT) image, a magnetic resonance (MR) image, and the like.

As used herein, expressions such as "at least one of," when preceding a list of elements, modify the entire list of elements and do not modify the individual elements of the list.

Figure 1:
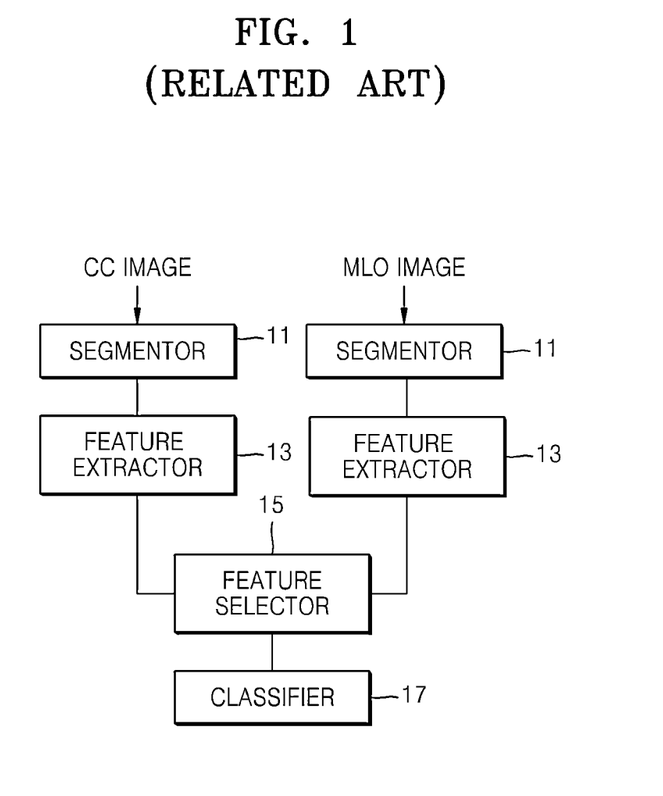
FIG. 1 is a block diagram of a CADx related art system for estimating whether a malignant tumor is in an object by using a cranio-caudal (CC) image and a mediolateral oblique (MLO) image.

FIG. 1 is a block diagram of a related art CADx system for estimating whether a malignant tumor is in an object by using a cranio-caudal (CC) image and a mediolateral oblique (MLO) image.

Referring to FIG. 1, in the related art CADx system, a segmentor 11 segments each of the CC image and the MLO image into regions of interest including a mass, and a feature extractor 13 extracts features from the regions of interest in the CC image and in the MLO image.

A feature selector 15 selects a feature commonly included in the CC image and the MLO image, and a classifier 17 analyzes the selected feature to determine whether a malignant tumor exists in an object.

According to the related art CADx system shown in FIG. 1, since the feature selector 15 selects only the feature commonly included in the CC image and the MLO image, an optimal feature suitable for determining whether a malignant tumor is in the object might not be selected from the features included in the CC image and the MLO image. Accordingly, there is a problem in that estimation accuracy of a malignant tumor may be reduced.

Figure 2:
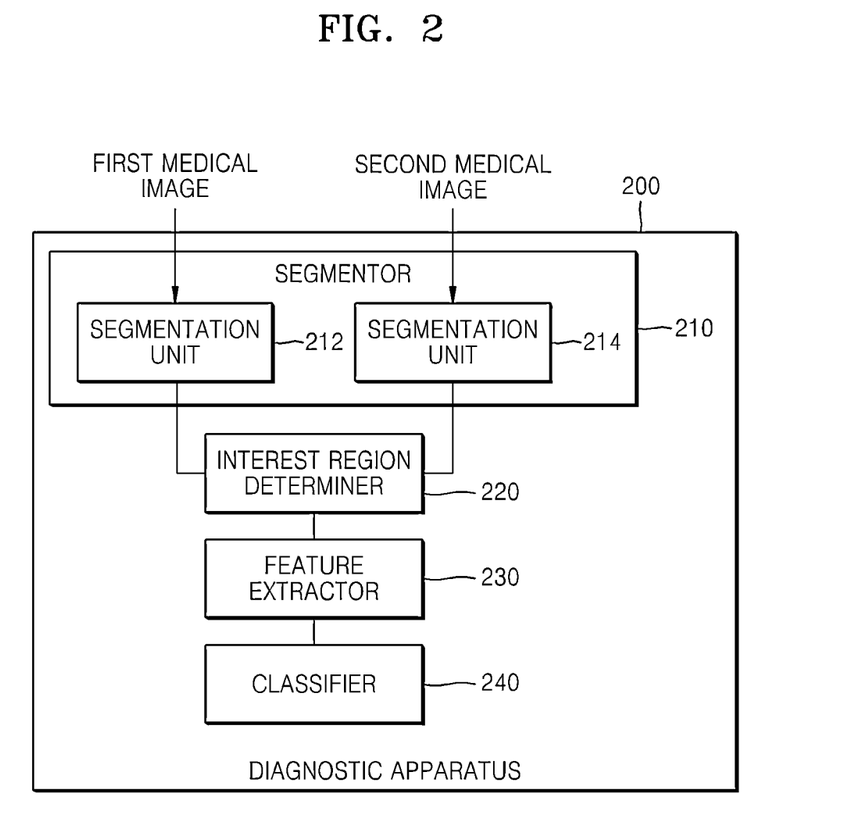
FIG. 2 is a block diagram of an apparatus for estimating a malignant tumor, according to an exemplary embodiment.

FIG. 2 is a block diagram of diagnostic apparatus 200 for estimating a malignant tumor, according to an exemplary embodiment.

Referring to FIG. 2, the apparatus 200 may include a segmentor 210, an interest region determiner 220, a feature extractor 230, and a classifier 240. The segmentor 210, the interest region pairing unit 220, the feature extractor 230, and the classifier 240 may be formed in a microprocessor.

Although FIG. 2 shows two segmentation units 212, 214, the segmentation units 212, 214 may be formed as one module or device.

A first medical image and a second medical image are input to the segmentor 210. The first medical image and the second medical image may be stored in a memory unit (not shown). Alternatively, although not shown in FIG. 2, the first medical image and the second medical image may be acquired by an image acquisition unit included in the apparatus 200.

The first medical image and the second medical image may be images captured by imaging an object in different directions. The first medical image may include a CC image of the breast, and the second medical image may include an MLO image of the breast.

The segmentor 210 segments the first medical image into at least one first ROI including a mass and segments the second medical image into at least one second ROI including a mass.

Each of the first ROI and the second ROI including a mass may be a region brighter than a surrounding region, may have almost constant density, and/or may have a certain shape having various sizes.

The first ROI and the second ROI may include a region suspected to include a mass that may be a false positive (FP) or a true positive (TP). A TP indicates a case where a suspected mass determined as a malignant tumor by the apparatus 200 is actually a malignant tumor, and an FP indicates a case where a suspected mass determined as a malignant tumor by the apparatus 200 is actually a benign tumor.

Figure 4A:
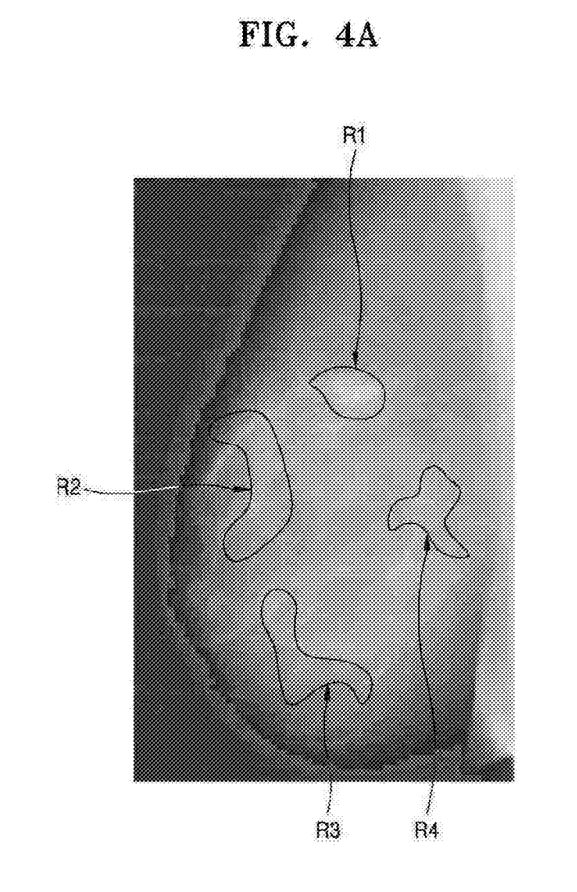
FIG. 4A illustrates a CC image in which first regions of interest are displayed.
Figure 4B:
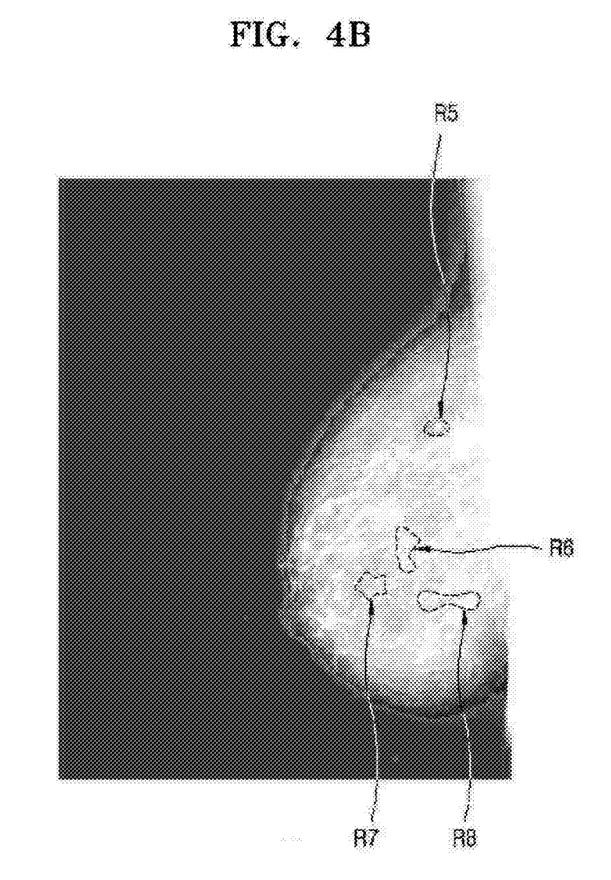
FIG. 4B illustrates an MLO image in which second regions of interest are displayed.

FIG. 4A illustrates a CC image in which four first regions of interest R1, R2, R3, and R4 are displayed, and FIG. 4B illustrates an MLO image in which four second regions of interest R5, R6, R7, and R8 are displayed.

Referring to FIG. 4A, the segmentor 210 may segment the CC image that is the first medical image into the four first regions of interest R1, R2, R3, and R4. Referring to FIG. 4B, the segmentor 210 may segment the MLO image that is the second medical image into the four second regions of interest R5, R6, R7, and R8. Although each of FIGS. 4A and 4B shows four regions of interest, various numbers of regions of interest may be included in the first medical image and/or the second medical image.

The segmentor 210 may segment the first medical image and the second medical image into regions of interest by using a fuzzy technique, a bilateral image subtraction technique, a multi-scale technique, or the like. Since the fuzzy technique, the bilateral image subtraction technique, and the multi-scale technique are known to one of ordinary skill in the art, a detailed description is omitted.

The segmentor 210 may acquire location information of each of the first regions of interest in the first medical image and of each of the second regions of interest in the second medical image. For example, the segmentor 210 may acquire the location information of each first ROI by using a location relationship between a nipple in the CC image and the first ROI and may acquire the location information of each second ROI by using a location relationship between a nipple in the MLO image and the second ROI.

The interest region determiner 220 may acquire a first matched ROI from one or more of the first regions of interest and acquire a second matched ROI from one or more of the second regions of interest, based on the location information of the first regions of interest and the location information of the second regions of interest.

The interest region determiner 220 may acquire the first matched ROI and the second matched ROI existing at the same location of the object. The existence at the same location of the object may indicate that a region of the object is commonly included and may indicate that a same mass of the object is included. One or more first regions of interest remaining by excluding the first matched ROI from the first regions of interest is a first non-matched ROI, and one or more second regions of interest remaining by excluding the second matched ROI from the second regions of interest is a second non-matched ROI.

Referring to FIGS. 4A and 4B, the interest region determiner 220 may acquire the first ROI R1 and the second ROI R5 as the first matched ROI and the second matched ROI, respectively. The other remaining first regions of interest R2, R3, and R4 of the CC image are included in the first non-matched regions of interest, and the other remaining second regions of interest R6, R7, and R8 of the MLO image are included in the second non-matched regions of interest.

Figure 5:
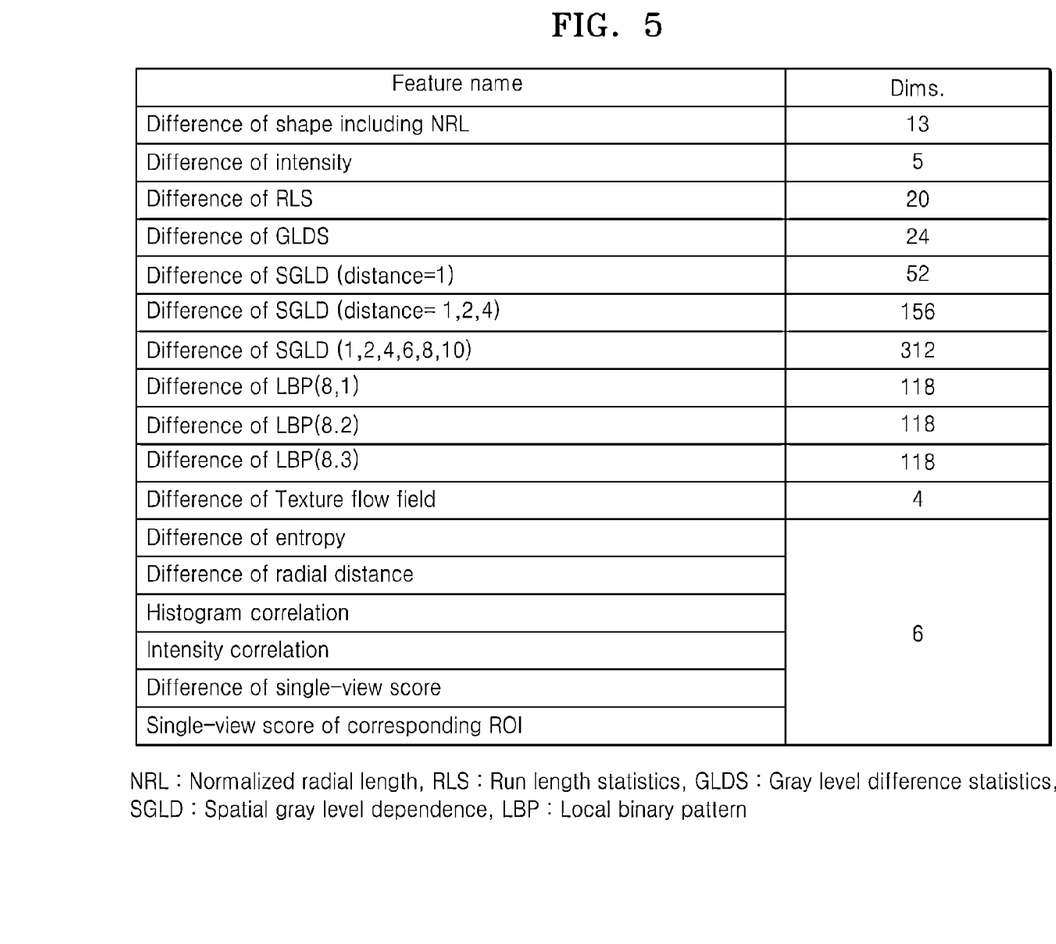
FIG. 5 is a table showing similar features, according to an exemplary embodiment.

The feature extractor 230 extracts at least one similar feature indicating a degree of similarity between the first matched ROI and the second matched ROI from the first matched ROI and the second matched ROI. The similar feature indicates a degree of similarity or a difference between the first matched ROI and the second matched ROI with respect to a shape, a size, density, and border smoothness. Types of the similar features are shown in FIG. 5.

The extraction of the similar feature may be performed using principle component analysis, linear discriminate analysis, a genetic algorithm (GA), or the like. Since the principle component analysis, the linear discriminate analysis, and the GA are known to one of ordinary skill in the art, a detailed description is omitted.

The classifier 240 generates malignant tumor information indicating whether a mass included in the first matched ROI and the second matched ROI is a malignant tumor, based on the similar feature extracted by the feature extractor 230. The malignant tumor information may include a determination result regarding whether a mass included in a medical image is a malignant tumor or a benign tumor, and a probability of accuracy of the determination result. "Dims." indicated in FIG. 5 may refer to a number of arguments that the similarity feature has.

The classifier 240 may determine a degree of similarity between the first matched ROI and the second matched ROI from the similar feature extracted by the feature extractor 230 and may determine that the mass included in the first matched ROI and the second matched ROI is a malignant tumor if the determined degree of similarity is greater than a reference value. The degree of similarity determined from the similar feature may be acquired by using various methods. For example, if the similar feature extracted by the feature extractor 230 include "Difference of intensity" which has a value of 5 and "Difference of RLS" which has a value of 3, the degree of similarity between the first matched ROI and the second matched ROI may be determined by multiplying a predetermined weighting values to a similarity value corresponding to the value 5 of "Difference of intensity" and a similarity value corresponding to the value 3 of "Difference of RLS" respectively, and summing the similarity value corresponding to the value 5 of "Difference of intensity" and the similarity value corresponding to the value 3 of "Difference of RLS" which have been multiplied by the predetermined weighting values. The similarity value corresponding to the value of "Difference of intensity," the similarity value corresponding to the value of "Difference of RLS" and the predetermined weighing values may be preset by a user. The classifier 240 may determine a probability of accuracy of a determination result according to a magnitude of the degree of similarity between the first matched ROI and the second matched ROI. For example, if the classifier 240 determines that a degree of similarity that is equal to or greater than 0.5 is a malignant tumor, a probability of accuracy of a determination result may increase as a degree of similarity that gets increasingly greater than 0.5.

The apparatus 200 is based on the concept that features between the first matched ROI and the second matched ROI are very similar when the first matched ROI and the second matched ROI of the first medical image and the second medical image are TP-TP. That is, a degree of similarity in a case of TP-TP is greater than that in a case of TP-FP or FP-FP.

Since the apparatus 200 compares and matches regions of interest included in the first medical image and the second medical image and extracts similar features between the matched regions of interest to determine whether a malignant tumor is in the object, the apparatus 200 may have improved accuracy in comparison with the related art CADx system for independently extracting features from the first medical image and the second medical image and analyzing the extracted features.

Figure 3:
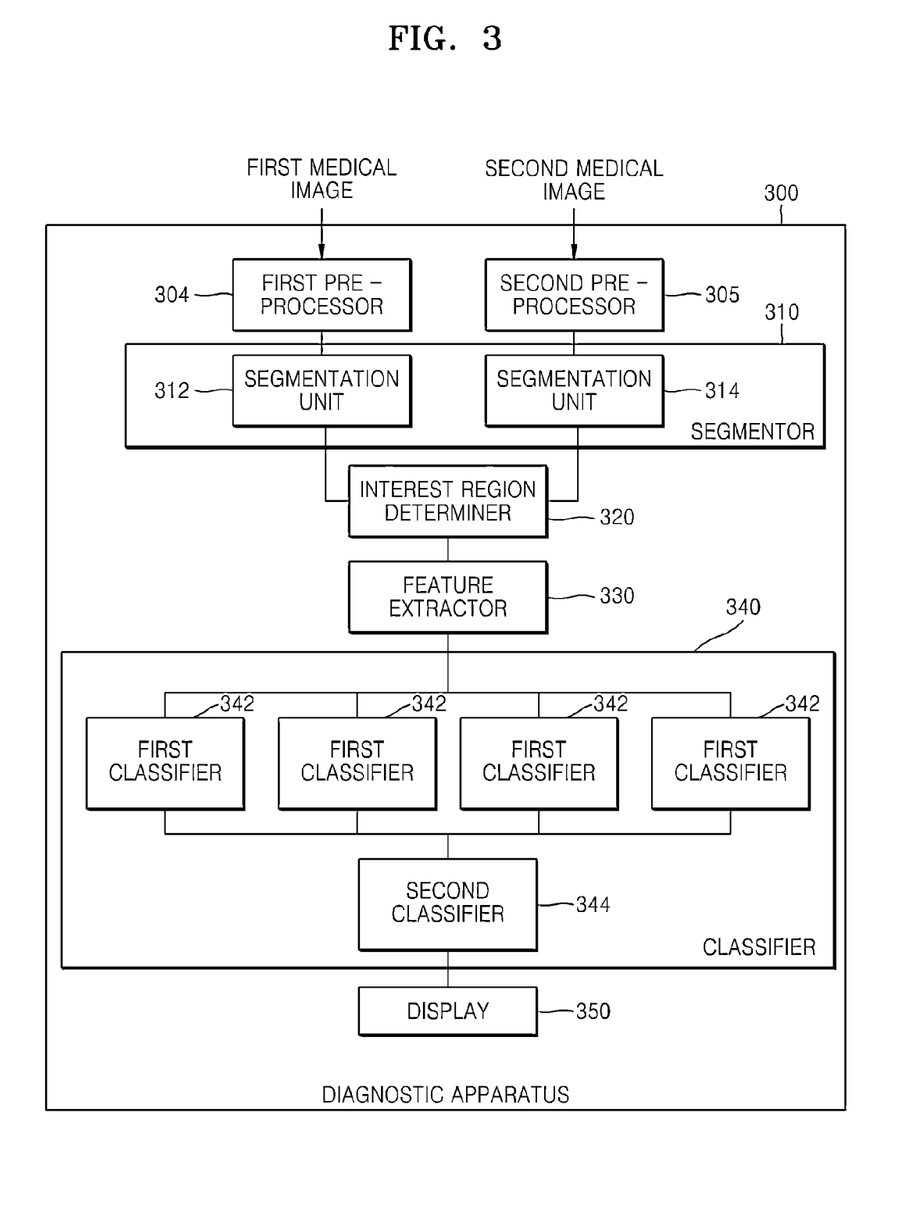
FIG. 3 is a block diagram of an apparatus for estimating a malignant tumor, according to an exemplary embodiment.

FIG. 3 is a block diagram of a diagnostic apparatus 300 for estimating a malignant tumor, according to an exemplary embodiment.

The apparatus 300 shown in FIG. 3 may include first and second pre-processors 304 and 305, a segmentor 310, an interest region determiner 320, a feature extractor 330, a plurality of first classifiers 342, a second classifier 344, and a display 350.

Although FIG. 3 shows the first and second pre-processors 304, 305, two segmentation units 312, 314, and a plurality of first classifiers 342, all or some of these components may be formed and may function as one module or device.

The first and second pre-processors 304 and 305 receive and pre-process a first medical image and a second medical image of an object. The pre-processing enhances a view of a tissue structure of the object by emphasizing a brightness difference between a mass and the like, which are included in the first medical image and the second medical image, and a surrounding background. The first and second pre-processors 304 and 305 may more clearly represent a structure of the object displayed in the first medical image and the second medical image by adjusting a contrast or brightness of the first medical image and the second medical image.

Since the segmentor, the interest region determiner, and the feature extractor are described above with reference to FIG. 2, a detailed description is omitted.

A classifier 340 may include the first classifiers 342 and the second classifier 344. The classifier 340 divides a similar feature extracted by the feature extractor 330 into groups. Each of the groups may include different features of the similar feature and may redundantly include a common feature.

A similar feature included in each group is input to each of the first classifiers 342. Each of the first classifiers 342 analyzes the input similar feature of the group to generate malignant tumor preparation information indicating whether a mass included in a first matched ROI and a second matched ROI is a malignant tumor or a benign tumor and a probability of accuracy of the determination result.

The second classifier 344 generates malignant tumor information by combining the pieces of malignant tumor preparation information generated by the first classifiers 342 and reliabilities of the first classifiers 342.

The reliability of each of the first classifiers 342 may be determined in a learning operation of the first classifiers 342.

The learning of a classifier indicates that parameters and the like of the classifier are changed so that the classifier may output a correct determination result after acquiring a determination result of the classifier by inputting similar features for which a result regarding the presence of a malignant tumor has been known to the classifier. The learning of a classifier may be repeatedly performed.

The apparatus 300 may calculate an error rate of each of N (where N is a natural number greater than 1) classifiers by learning the N classifiers and select M (where M is a natural number less than N) classifiers as the first classifiers 342 based on the calculated error rates. The reliability of each of the first classifiers 342 may be acquired based on the error rate of each of the first classifiers 342.

The second classifier 344 may generate malignant tumor information by multiplying the determination results of the first classifiers 342 or probabilities of the determination results by the reliabilities of the first classifiers 342 as weights.

For example, a determination result of each first classifier is derived as a numeric value between 0 and 1, where 0 indicates that a probability of a malignant tumor is 0%, and 1 indicates a probability of a malignant tumor is 100%. If a determination result of a classifier 1-1 of which reliability is 0.25 is 0.4, a determination result of a classifier 1-2 of which reliability is 0.3 is 0.8, and a determination result of a classifier 1-3 of which reliability is 0.35 is 0.7, the second classifier 344 may generate malignant tumor information as (0.25*0.4)+(0.3*0.8)+(0.35*0.7).

The feature extractor 330 may extract features from a first non-matched ROI and a second non-matched ROI. The classifier 340 may analyze the extracted features to determine whether a mass included in the first non-matched ROI is a malignant tumor and whether a mass included in the second non-matched ROI is a malignant tumor.

The display 350 displays a mark on a mass determined as a malignant tumor in the first medical image and the second medical image so that a medical professional can easily identify a region in which the malignant tumor exists.

The display 350 may display a first mark on a position corresponding to the first non-matched ROI in the first medical image when a mass included in the first non-matched ROI is determined as a malignant tumor and may display the first mark on a position corresponding to the second non-matched ROI in the second medical image when a mass included in the second non-matched ROI is determined as a malignant tumor. When a mass included in the first matched ROI and the second matched ROI is determined as a malignant tumor, the display 350 may display a second mark visually different from the first mark on a position corresponding to each of the first matched ROI and the second matched ROI in the first medical image and the second medical image.

Figure 6:
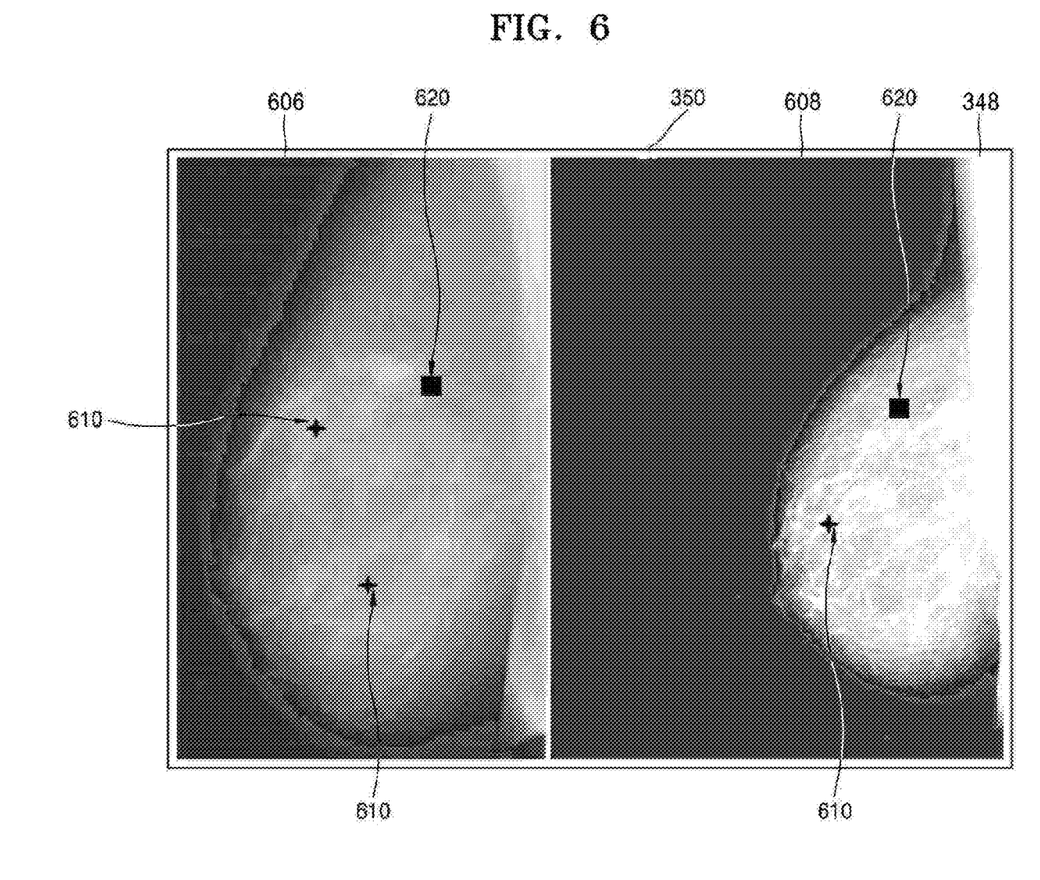
FIG. 6 illustrates a CC image and an MLO image displayed on a display, according to an exemplary embodiment.

FIG. 6 illustrates a CC image 606 and an MLO image 608 displayed on a screen 348 of the display 350, according to an exemplary embodiment.

Referring to FIG. 6, the display 350 displays a star-shaped mark 610 in the first non-matched ROI and the second non-matched ROI including a mass determined as a malignant tumor and displays a square-shaped mark 620 in the first matched ROI and the second matched ROI including a mass determined as a malignant tumor.

When a mass included in the matched regions of interest is determined as a malignant tumor, a probability that the mass is TP is very high, and, thus, another mark different from a mark on the non-matched regions of interest is displayed so that a medical professional can easily identify a region having a high probability of the presence of a malignant tumor.

Figure 7:
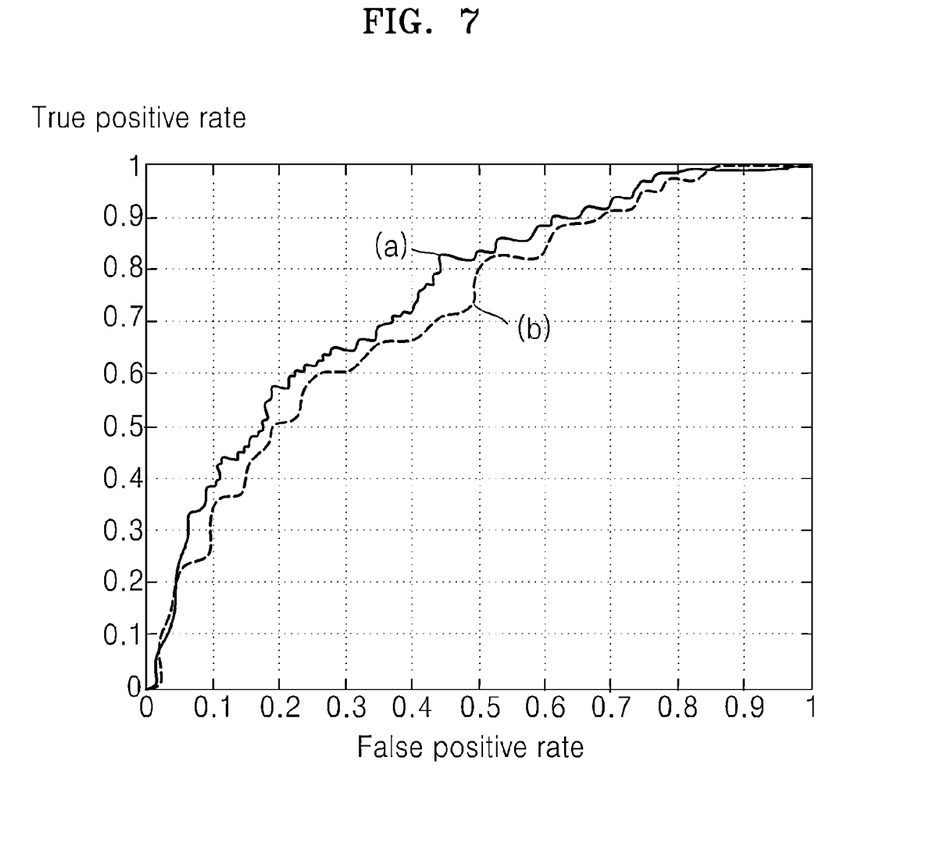
FIG. 7 is a graph for describing a difference between the apparatus for estimating a malignant tumor according to an exemplary embodiment and the related art CADx system.

FIG. 7 is a graph for describing a difference between an exemplary embodiment and the related art CADx system.

FIG. 7 shows a receiver operating characteristic (ROC) curve (a) of the diagnostic apparatus according to an exemplary embodiment and an ROC curve (b) of the related art CADx system. The ROC curve is expressed as a TP rate versus an FP rate. In an ROC curve, analysis accuracy of a medical image is excellent when an area under the ROC (AUC) is large.

Referring to FIG. 7, since an AUC of the apparatus according to an exemplary embodiment is larger than an AUC of the related art CADx system, accuracy of the apparatus according to an exemplary embodiment is excellent.

Figure 8:
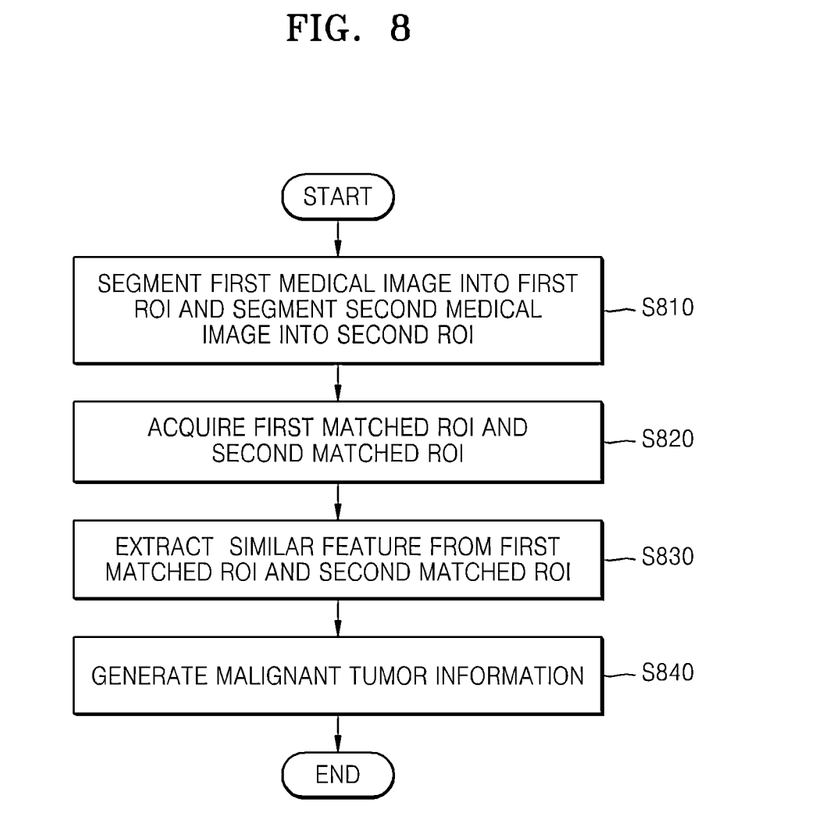
FIG. 8 is a flowchart illustrating a method of estimating a malignant tumor, according to an exemplary embodiment.

FIG. 8 is a flowchart illustrating a method of estimating a malignant tumor, according to an exemplary embodiment. Referring to FIG. 8, the method includes operations performed by the diagnostic apparatus described above.

In operation S810, the diagnostic apparatus segments a first medical image into a first ROI including a mass and segments a second medical image into a second ROI including a mass. The apparatus may perform pre-processing to adjust a contrast or brightness of the first medical image and the second medical image before segmenting the first medical image and the second medical image.

In operation S820, the apparatus acquires a first matched ROI from one or more of the first regions of interest and a second matched ROI from one or more of the second regions of interest, based on location information of the first regions of interest and location information of the second regions of interest.

In operation S830, the apparatus extracts a similar feature indicating a degree of similarity between the first matched ROI and the second matched ROI, from the first matched ROI and the second matched ROI.

In operation S840, the apparatus generates malignant tumor information indicating whether a mass included in the first matched ROI and the second matched ROI is a malignant tumor, based on the similar feature. The malignant tumor information may include a determination result whether the mass included in the first matched ROI and the second matched ROI is a malignant tumor or a benign tumor, and a probability of accuracy of the determination result.

The exemplary embodiments may be written as computer programs and may be implemented in general-use computers that execute the programs using a computer-readable recording medium. Examples of the computer-readable recording medium include storage media, such as magnetic storage media (e.g., ROM, floppy disks, hard disks, etc.), optical recording media (e.g., CD-ROMs, or DVDs), and carrier waves (e.g., transmission through the Internet).

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a malignant tumor, the apparatus comprising:
    a segmentor configured to segment a first medical image of an object into a first region of interest (ROI) including a mass and a second medical image of the object into a second ROI including a mass;
    an interest region determiner configured to acquire a first matched ROI and a second matched ROI, which is matched to the first matched ROI based on location information of the first ROI and the second ROI, respectively;
    a feature extractor configured to extract similar features indicating a degree of similarity between the first matched ROI and the second matched ROI, from the first matched ROI and the second matched ROI; and
    a classifier configured to generate malignant tumor information indicating whether the mass included in the first matched ROI and the second matched ROI is the malignant tumor, based on the extracted similar features,
    wherein the classifier comprises:
        a plurality of first classifiers configured to generate probabilities of accuracy of determination that the mass included in the first matched ROI and the second matched ROI is the malignant tumor by analyzing each of the similar features; and a second classifier configured to generate the malignant tumor information by multiplying the probabilities by respective reliabilities of the plurality of first classifiers as weight.

2. The apparatus of claim 1, wherein the interest region determiner is configured to acquire the first matched ROI and the second matched ROI which commonly include a same region or same mass of the object in the first and second medical images.

3. The apparatus of claim 1, wherein the respective reliabilities of the plurality of first classifiers are determined in a learning operation of the plurality of first classifiers.

4. The apparatus of claim 1, wherein the classifier is configured to determine a degree of similarity between the first matched ROI and the second matched ROI from the extracted similar feature, and
to determine that the mass included in the first matched ROI and the second matched ROI is the malignant tumor if the degree of similarity is greater than a reference value.

5. The apparatus of claim 1, further comprising:
a pre-processor configured to pre-process the first medical image and the second medical image to adjust a contrast or a brightness of the first medical image and the second medical image.

6. The apparatus of claim 1, wherein the segmentor is configured to segment the first medical image into a plurality of first regions of interest each including the mass and the second medical image into a plurality of second regions of interest each including the mass;
the feature extractor is configured to extract a first feature from a first non-matched ROI, which is included into the plurality of first regions of interest and is different from the first matched ROI, and a second feature from a second non-matched ROI, which is included into the plurality of second regions of interest and is different from the second matched ROI, and
the classifier is configured to determine whether the mass included in the first non-matched ROI is the malignant tumor, based on the first feature, and whether the mass included in the second non-matched ROI is the malignant tumor, based on the second feature.

7. The apparatus of claim 6, further comprising:
a display which displays a first mark on a first image portion corresponding to the first non-matched ROI in the first medical image when the mass included in the first non-matched ROI is determined as the malignant tumor,
displays the first mark on a second image portion corresponding to the second non-matched ROI in the second medical image when the mass included in the second non-matched ROI is determined as the malignant tumor, and
displays a second mark visually different from the first mark on a third image portion corresponding to each of the first matched ROI and the second matched ROI in the first medical image and the second medical image, respectively, when the mass included in the first matched ROI and the second matched ROI is determined as the malignant tumor.

8. The apparatus of claim 1, wherein the first medical image includes a cranio-caudal (CC) image of a breast, and the second medical image includes a mediolateral oblique (MLO) image of the breast.

9. The apparatus of claim 8, wherein the interest region determiner is configured to acquire the location information of the first ROI by using a location relationship between a nipple in the CC image and the first ROI and of the second ROI by using a location relationship between the nipple in the MLO image and the second ROI.

10. A method of estimating a malignant tumor, the method comprising:
segmenting a first medical image of an object into a first region of interest (ROI) including a mass and a second medical image of the object into a second ROI including a mass;
acquiring a first matched ROI and a second matched ROI which matches the first matched ROI, based on location information of the first ROI and the second ROI, respectively;
extracting similar features indicating a degree of similarity between the first matched ROI and the second matched ROI, from the first matched ROI and the second matched ROI; and
generating malignant tumor information indicating whether a mass included in the first matched ROI and the second matched ROI is the malignant tumor, based on the extracted similar features,
wherein the generating the malignant tumor information comprises:
dividing the extracted similar features into groups;
generating, by respective classifiers, probabilities of accuracy of determination that the mass included in the first matched ROI and the second matched ROI is the malignant tumor by analyzing the similar features included in each of the groups; and
generating the malignant tumor information by multiplying the probabilities by respective reliabilities of the classifiers as weight.

11. The method of claim 10, wherein the acquiring the first matched ROI and the second matched ROI comprises acquiring the first matched ROI and the second matched ROI which commonly include a same region or same mass of the object.

12. The method of claim 10, wherein the respective reliabilities of the classifiers are determined in a learning operation of the classifiers.

13. The method of claim 10, wherein the generating the malignant tumor information comprises:
determining a degree of similarity between the first matched ROI and the second matched ROI from the extracted similar feature; and
determining that the mass included in the first matched ROI and the second matched ROI is the malignant tumor if the degree of similarity is greater than a reference value.

14. The method of claim 10, further comprising:
pre-processing the first medical image and the second medical image to adjust a contrast or a brightness of the first medical image and the second medical image.

15. The method of claim 10, further comprising:
segmenting the first medical image into a plurality of first regions of interest each including the mass;
segmenting the second medical image into a plurality of second regions of interest each including the mass;
extracting a first feature from a first non-matched ROI which is included in the plurality of first regions of interest and is different from the first matched ROI;
extracting a second feature from a second non-matched ROI which is included in the plurality of second regions of interest and is different from the second matched ROI;
determining whether the mass included in the first non-matched ROI is the malignant tumor, based on the first feature; and determining whether the mass included in the second non-matched ROI is a malignant tumor, based on the second feature.

16. The method of claim 15, further comprising:

displaying a first mark on a first image portion corresponding to the first non-matched ROI in the first medical image when the mass included in the first non-matched ROI is determined as the malignant tumor and on a second image portion corresponding to the second non-matched ROI in the second medical image when the mass included in the second non-matched ROI is determined as the malignant tumor; and displaying a second mark visually different from the first mark on a third image portion corresponding to each of the first matched ROI and the second matched ROI in the first medical image and the second medical image, respectively, when the mass included in the first matched ROI and the second matched ROI is determined as the malignant tumor.

17. The method of claim 10, wherein the first medical image includes a cranio-caudal (CC) image of a breast, and the second medical image includes a mediolateral oblique (MLO) image of the breast.

18. The method of claim 17, further comprising:

acquiring the location information of the first ROI based on a location relationship between a nipple in the CC image and the first ROI; and acquiring the location information of the second ROI based on a location relationship between the nipple in the MLO image and the second ROI.

19. A non-transitory computer-readable storage medium having stored therein program instructions, which when executed by a computer, cause the computer to perform the method of claim 10.

* * * * *